United States Patent [19]

Troutner

[11] Patent Number: 4,573,962
[45] Date of Patent: Mar. 4, 1986

[54] CASSETTE DRAWER ASSEMBLY FOR PHOTOACTIVATION PATIENT TREATMENT SYSTEM

[75] Inventor: Vernon H. Troutner, St. Petersburg, Fla.

[73] Assignee: Extracorporeal Medical Specialties, Inc., King of Prussia, Pa.

[21] Appl. No.: 665,817

[22] Filed: Oct. 29, 1984

[51] Int. Cl.$^4$ ............................................ A61M 37/00
[52] U.S. Cl. ........................................................ 604/6
[58] Field of Search ...................... 604/4, 5, 6, 20, 259

[56] References Cited

U.S. PATENT DOCUMENTS

| | | | |
|---|---|---|---|
| 4,398,906 | 8/1983 | Edelson | 604/6 |
| 4,425,116 | 1/1984 | Bilstad | 604/6 X |
| 4,481,827 | 11/1984 | Bilstad | 604/6 X |

*Primary Examiner*—Harland S. Skogquist
*Attorney, Agent, or Firm*—Mark A. Hofer

[57] ABSTRACT

Cassette drawer assembly for receiving an irradiation cassette wherein patient blood is irradiated to photoactivate a reagent in contact therewith, said irradiated blood being returned to the patient as part of the complete treatment.

5 Claims, 6 Drawing Figures

CASSETTE DRAWER ASSEMBLY FOR PHOTOACTIVATION PATIENT TREATMENT SYSTEM

FIELD OF THE INVENTION

This invention relates to the field of treating cells with photoactivatable compounds and radiation which activates the compound thereby affecting the cells and specifically, relates to clinically useful systems for the extracorporeal treatment of blood cells, especially leukocytes, with UV radiation.

BACKGROUND OF THE INVENTION

It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects to patients including the functional impairment of bodily organs, leukocyte mediated autoimmune diseases and leukemia related disorders many of which often ultimately result in fatality.

U.S. Pat. Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of U.V. radiation. It is believed that covalent bonding results between the psoralen and the lymphocyte nucleic acid thereby effecting metabolic inhibition of the thusly treated cells. Following extracorporeal radiation, the cells are returned to the patient where they are thought to be cleared by natural processes but at an accelerated pace believed attributable to disruption of membrane integrity, alteration of DNA within the cell, or the like conditions often associated with substantial loss of cellular effectiveness or viability.

Although a number of photoactivatable compounds in the psoralen class are known, 8-methoxy psoralen is presently the compound of choice. An effective radiation for this compound, and many psoralens in general, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum will be necessary. Suitable selection of radiation sources will, of course, increase treatment efficiency and is contemplated as an obvious optimization procedure for use with the inventions disclosed herein.

Although Edelson's methods have been experimentally shown to provide great relief to patients suffering from leukocyte mediated diseases, numerous practical problems remained requiring solutions. In particular, Edelson fails to provide a suitable apparatus for applying radiation to the cells, e.g. via a treatment station, in an economical and efficacious manner, or a system for incorporating a treatment station providing for the treatment of a patient in a clinically acceptable format.

Conventional techniques for photoactivating compounds associated with cells have relied on a plurality of devices including flasks, filtration columns, spectrophotometer cuvettes, and petri dishes. The sample to be irradiated is added to the containers and the container placed adjacent to the radiation source. Such systems tend to be laboratory curiosities as they fail to provide the necessary safeguards intrinsically necessary where patient bodily fluids are concerned, particularly since these fluids must be returned to the patient thereby necessitating strict avoidance of contamination. Further, such methods tend to be volume limited, are characterized by many mechanical manipulations and are generally unacceptable from a clinical and regulatory viewpoint. It is an object of the present invention to provide methods and apparatus suitable for use with the Edelson methods to overcome the limitations associated with the conventional expedients.

Copending application U.S. Ser. No. 650,602 of Taylor describes a preferred form of a practical device for coupling the radiation provided by commercially available light sources, such as the so-called "black-light" fluorescent tubes, to cells for treatment by Edelson's photoactivated drug methods. In summary, the disposable cassette described therein comprises a plurality of fluorescent tube-like light sources such as the U.V.A. emitting Sylvania F8TS/BLB bulb, which are individually, coaxially mounted in tubes of larger diameter which are, in turn, coaxially mounted in sealing arrangement within second outer tubes of even larger diameter thereby forming a structure having two generally elongated, cylindrical cavities about each radiation source. The inner cavity preferably communicates with the atmosphere thereby facilitating cooling of the radiation source. The second tube forming the outer cavity further comprises inlet and outlet means for receiving and discharging, respectively, the cells to be irradiated. A plurality of these structures are "ganged" and suitable connections made between inlets and outlets of adjacent members to provide for serpentine flow of cells through each outer cavity. Thus, continuous flow of the cells through the plurality of cavities surrounding the centrally disposed radiation sources facilitates thorough treatment of the cells. Additional, detailed description of the Taylor device may be obtained by direct reference to the abovesaid application.

To be fully practical, however, the Taylor device requires a clinically acceptable instrument to house the device and to provide the cells to be treated in an appropriate form. It is an object of the present invention to provide such a device.

To date and for clinical use-approval related purposes, the Edelson methods have been performed utilizing a generally impractical and unwieldy apparatus consisting of a large, desk-size metal box containing a series of flexible, relatively transparent plastic bags through which patient blood was pumped. As the blood flowed through each bag, it was irradiated on either side by a plurality of ultraviolet emitting, standard sized, "fluorescent" type tubes housed within the box. Blood flow was generated by means of a separate pump located nearby and connected to the plastic bags as well as source and drain reservoirs by flexible tubing.

Prior to treatment, it has been found preferable to perform leukocyte enriching operations for the purpose of removing substantial portions of red blood cells from the treatment circuit. With the preliminary experimental apparatus, leukocyte enrichment was obtained by centrifuging batch quantities of blood in large volume centrifuge tubes and then dispensing the supernatant plasma into the source bag for treatment. Thus, the Edelson methods have been carried out to date via a cumbersome series of labor intensive, error-prone steps, often exposing the patient's blood to numerous potential sources of contamination during its travels to and from equipment, none of which was designed to optimize the Edelson procedures. Excessive time delays and extensive mechanical manipulations were further exacerbated by the typically divergent locations of various pieces of equipment, necessitated by their space consuming construction. These considerations have resulted in lengthy treatment times and, due to the numerous physical manipulations required, have concommittantly and unacceptably increased the risk of loss or contamination of patient's blood.

It is an object of the present invention to provide methods and apparatus for increasing patient safety thereby also raising his comfort level as well as meeting regulatory acceptability standards.

It is another related object to provide a complete treatment system which contains all the elements necessary for the withdrawal, separation, and treatment of the patient's blood in a compact and clinically acceptable size and to provide the system in a mobile and automated format thereby reducing the risk of inadvertent contamination while concurrently facilitating the ease with which treatment may be given.

It is still another related object to provide a suitably automated instrument which can be monitored and operated by less trained personnel thereby lowering treatment costs in accordance with the recently enacted fiscal policies.

It is yet still another object to provide a treatment system suitable for use in the clinical arena whereby the acceptability of the Edelson procedures may be augmented so that a greater number of patients may be meaningfully treated.

BRIEF DESCRIPTION OF THE DRAWINGS

These and still other objects of the invention will become apparant upon study of the accompanying drawings wherein.

SUMMARY OF THE INVENTION

Methods are provided for extracorporeally photoactivating a photoactivatable reagent in contact with blood cells comprising the steps of collecting and separating on a continuous basis blood from a patient while the patient is connected to the apparatus, returning undesired blood portions obtained during separation, disconnecting the patient from the treatment system while the desired portion is photoactivatably treated whereupon the thusly treated cells are returned to the patient. The patient's safety and the procedural optimization of various aspects of the photoactivation treatment is advantageously accomplished by breaking the entire procedure down into three operational phases or modes. The apparatus, in the first mode, seeks to collect and separate blood on a continuous basis as it is withdrawn from the patient and to return unwanted portions to the patient while the patient remains connected to the apparatus. Thereafter, prior to energizing the irradiation sources for photoactivating the photoactivatable reagent in contact with the desired blood portion, the patient is disconnected from the machine thereby physically and electrically isolating him (or her) from the energizing high voltage, a potential source of harm. Following photoactivation, the treated cells may then be facilely returned to the patient utilizing a variety of techniques, the preferred being a simple drip chamber gravity feed infusion line.

Figure 1:
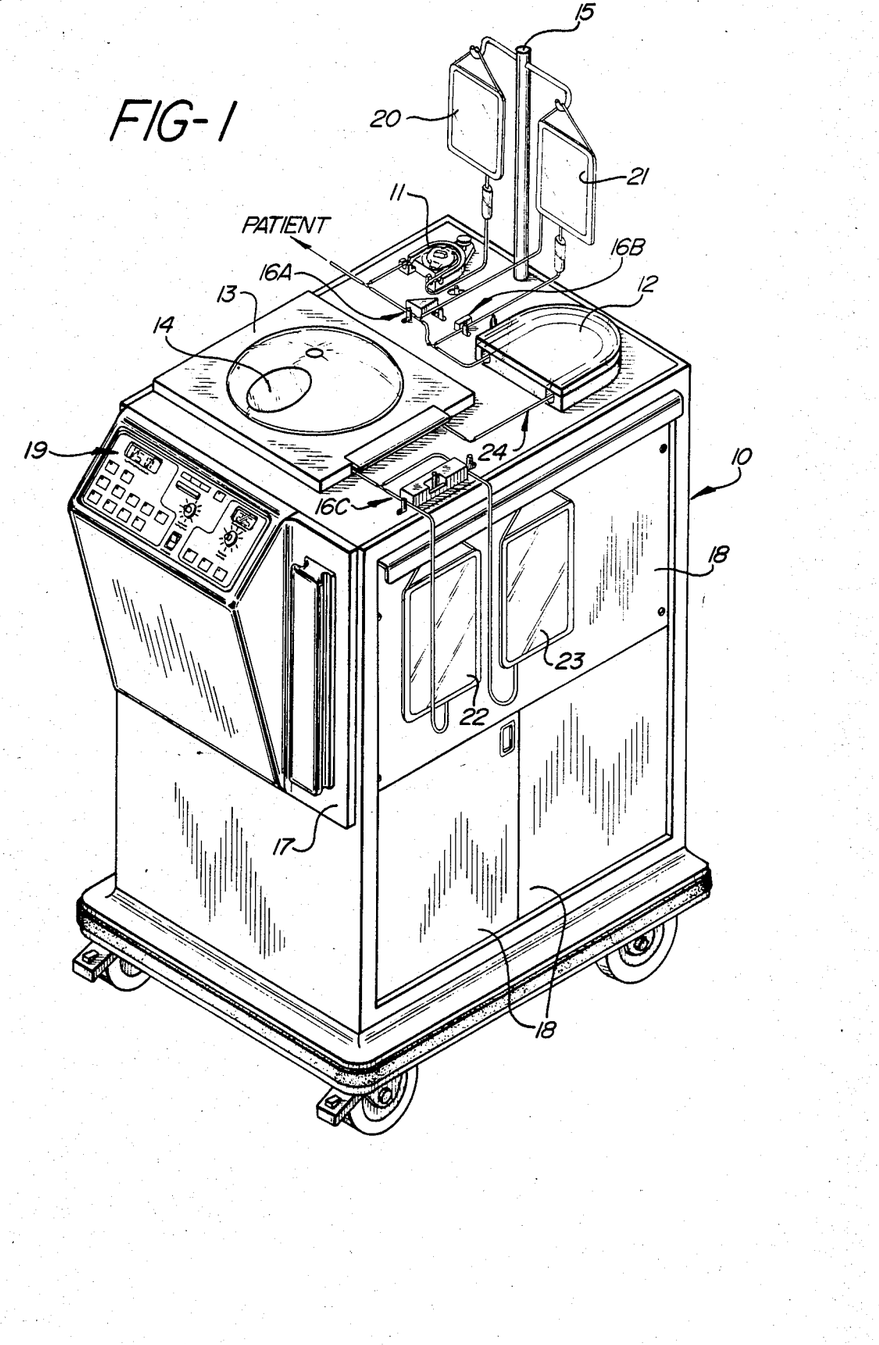
FIG. 1 illustrates a preferred configuration of the system in the collection and separation mode.
Figure 2:
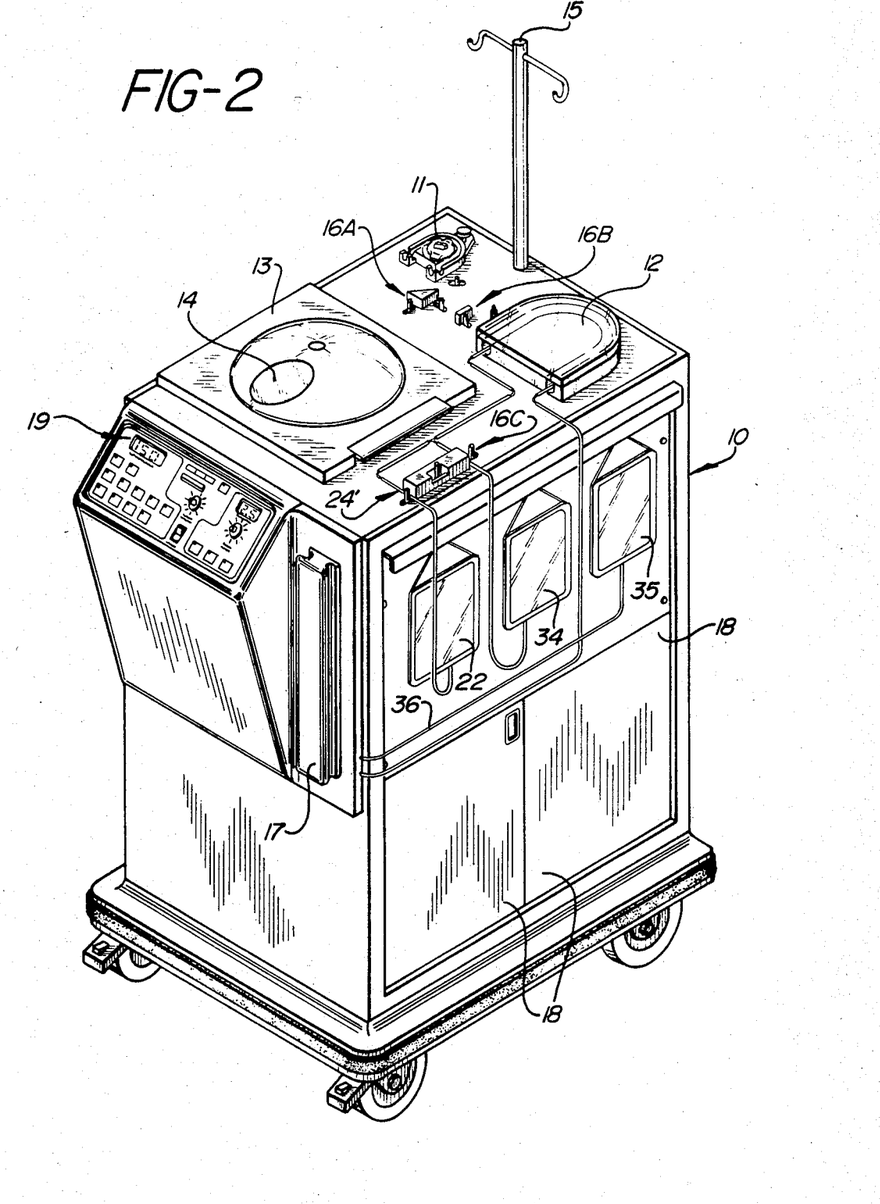
FIG. 2 depicts the system in the treatment mode.
Figure 3:
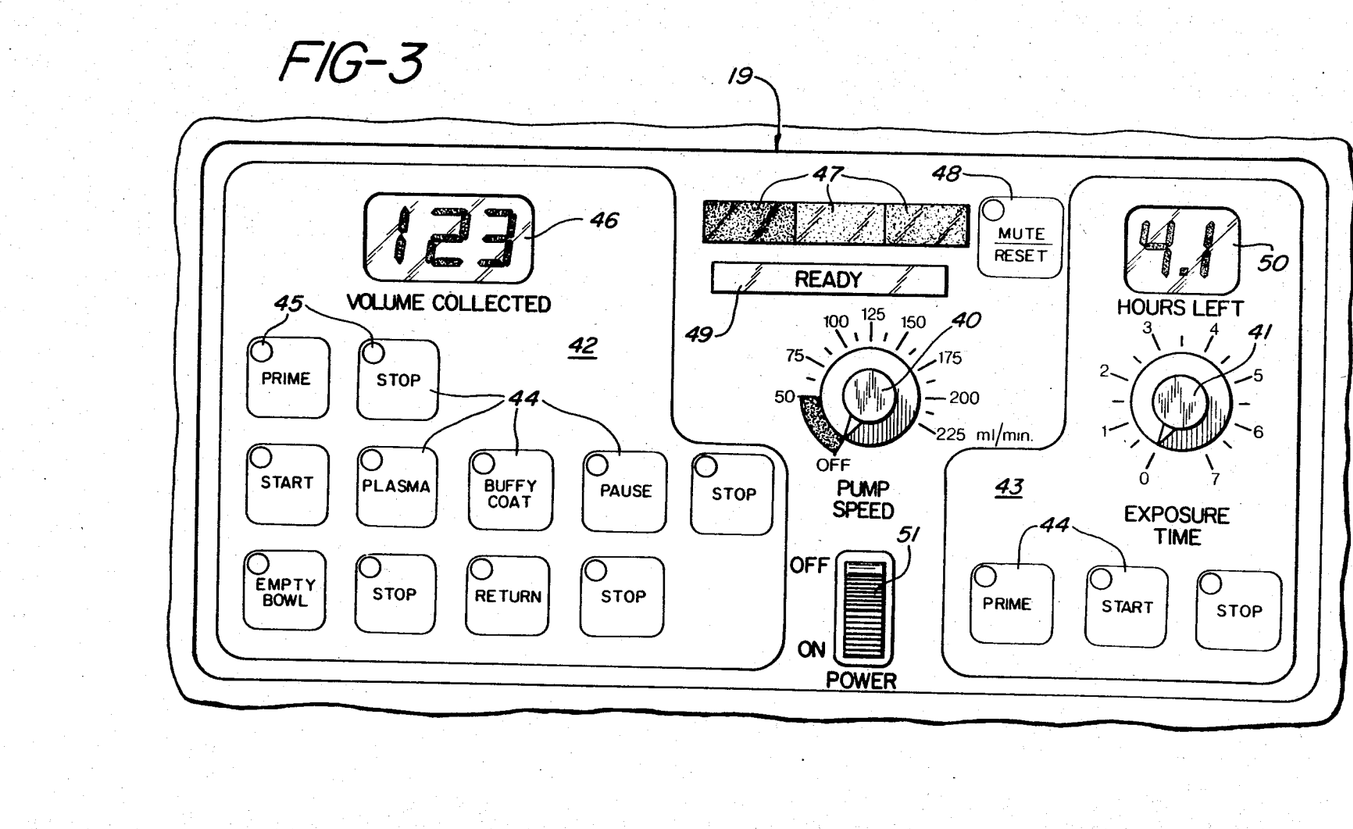
FIG. 3 shows the control panel for the system.

FIGS. 1, 2, and 3 show various aspects of the apparatus developed by the assignee hereof for extracorporeally treating a patient based in part upon the scientific discoveries of Edelson. The design, construction and operation of the apparatus 10 is the result of a number of separate inventions some of which form the subject matter of copending commonly assigned applications including U.S. Ser. No. 665,834 to Goss entitled "Three Phase Irradiation Treatment Process"; U.S. Ser. No. 665,831 to King entitled "Electronic Control Methods for Puvapheresis Apparatus"; U.S. Ser. No. 665,827 to Troutner entitled "Valve Apparatus for Photoactivation Patient Treatment System"; U.S. Ser. No. 665,833 to King et al. entitled "Patient Photopheresis Treatment Apparatus and Method"; and U.S. Ser. No. 665,826 to Hartranft entitled "Pump Monitor for Photoactivation Patient Treatment System", the relevant parts of which are fully incorporated herein by reference.

The operation of the device and performance of the methods can be divided into three basic phases or modes, depicted in part by FIGS. 1 and 2. The first phase is shown substantially in FIG. 1 wherein the patient is connected at the location shown, such as by veni-puncture or the like methods well-known and developed to a high degree in the dialysis arts. Patient blood, as it flows to the apparatus 10 (alternately referred to herein as the puvapheresis apparatus or system) is preferably infused, under control of pump 11, with an anti-coagulant agent contained in container 20 hung from stand 15. Control of the flow of patient blood to the remainder of apparatus 10 is controlled largely by clamping means 16a which has the dual function of also controlling flow in the reverse direction as well as flow to return container 21; clamp on 16a acting as an "or" valve. Normally the blood flows through tubing 24 through blood pump 12 into a continuous centrifuge 13. This continuous centrifuge, available commercially from suppliers such as Dideco and others, is preferably capable of continuously separating blood based on the differing densities of the individual blood components. "Continuously", as used herein means that as blood flows into the centrifuge through line 24, it accumulates within the rotating centrifuge bowl and is separated so that low density components are emitted after a certain minimum volume has been reached within the centrifuge bowl and as additional blood is added. Thus, the continuous centrifuge in effect acts as a hybrid between a pure on-line system and a pure batch system. This occurs because the centrifuge bowl has a capacity to hold most, if not all, of the most dense portion, typically erythrocytes or red blood cells while emitting lower density portions such as plasma and leukocytes (white blood cells) as whole blood is continuously added. At some point, however, the reservoir volume of the centrifuge is filled with the higher density components and further separation cannot be effectively obtained. Prior to that point, the operator, by viewing the uppermost portion of the centrifuge bowl through magnifying observation port 14 of the centrifuge cover, can detect qualitatively when the centrifuge emits plasma (as opposed to priming solution), leukocyte enriched portions and nonleukocyte enriched portions, e.g. erythrocytes. Based on the operator's observations, he or she enters through control panel 19 (specifically via panel portion 42) the identification of the individual blood portions as they are emitted from the centrifuge. Based on this information entered by keys 44 (e.g. plasma, buffy coat or leukocyte enriched portion) on control panel 19, (shown in FIG. 3) the apparatus 10 controls valve mechanism 16c to direct the leukocyte enriched portion and a predetermined volume of plasma into plasma-leukocyte enriched container 22 while excess plasma, air, priming fluids, erythrocytes etc. are directed to container 23.

Once the centrifuge is no longer capable of further separation due to the attainment of its capacity, the operator directs that the bowl be emptied (see FIG. 3) by suitable data key entry and the contents of container 23 and centrifuge 13 are advantageously pumped into return container 21 by means of pump 12 under the control of valves 16a and c. The foregoing steps may be repeated a number of times or cycles before the desired volume of leukocyte enriched blood and plasma is obtained for further treatment, in each instance the undesired portions being first collected in container 23 and then pumped to return container 21.

Between cycles, the erythrocyte enriched blood portion (actually nonleukocyte enriched fluid as it may also contain some priming fluid and anticoagulant) having been pumped into return bag 21 is gravity fed back to the patient through a drip infusion operation controlled by valve 16b. It is preferred that gravity feed be employed rather than pumping the blood back to the patient, such as by blood pump 12, in order to avoid potential pressurization problems at the infusion insertion site at the patient, and also to avoid foaming or other air related dangers.

As may be already appreciated, when initially set up, line 24 may be expected to contain sterilized air which is preferably removed by suitable priming operations utilizing the anti-coagulation agent in container 20; both the air and the priming solution being collected in container 23.

Also to be noted is the preferred predetermination of the desired leukocyte enriched volume and plasma volume to be collected within container 22 as well as the number of cycles to be employed to collect same. These volumes are selected largely in accordance with the individual volume capacities of the containers as well as the treatment cassette to be described later. Accordingly, these volumes are selected to preferably optimize handling efficiency and to ensure patient safety. For instance, one preferred selection would include approximately 250 ml total buffy coat or leukocyte enriched portion and 300 ml of plasma to be collected within container 22. This might require any number of cycles preferably on the order of say three or four bearing in mind that the more cycles that are selected, the lower the total volume of blood withdrawn from the patient at any one time, within minimum capacity limits of the centrifuge bowl, thus increasing the patient's capacity to withstand temporary blood volume depletions. Also, a greater number of cycles will permit more discriminating selection of leukocyte enriched blood as it is emitted from the centrifuge. The buffy coat and plasma volumes as well as the number of cycles are typically physician selected and accordingly, the controls governing the selections are preferably placed within the apparatus 10, such as behind doors 18 where their inadvertent alteration may be avoided especially since no operator interaction is required with respect to these data inputs.

Referring now to FIG. 2, a second tubing set or mode of the apparatus 10 is shown wherein the leukocyte enriched container 22 is connected via tubing line 24' through valve 16c to blood pump 12 to the treatment cassette behind door 17 with a return line 36 leading to reservoir container 35. The tubing set for the second mode will also preferably include container 34 for providing a priming solution for evacuating air contained within tubing set 24' and the cassette irradiation treatment module described in the copending application of Taylor, U.S. Ser. No. 650,602. In brief summary, the Taylor cassette comprises a plurality of ganged cylindrical cavities each of which is concentrically mounted around an irradiation source in turn powered by apparatus 10.

In operation, and with respect to FIG. 3, the exposure time on the right hand portion of the panel 43 is set in accordance with physician determined criteria via knob 41. The central control means of the apparatus 10, calculates and displays (50) via central processing unit and memory stored software, the time remaining at the onset of irradiation treatment and as the treatment progresses. Section 43 of the control panel also includes three operator controlled entry data keys 44 whereby the first step, PRIME, may be initiated whereupon the priming solution from container 34 is pumped via blood pump 12 through tubing set 24' and the treatment cassette emptying into reservoir 35. Thereafter, the operator, by pushing START in section 43, initiates actual photoirradiation treatment whereupon the leukocyte enriched portion of the blood collected within container 22 is pumped through tubing set 24' in accordance with suitably altered valve 16c through blood pump 12 to the treatment cassette and return line 36 to reservoir 35.

The treatment cassette container assembly 17 further comprises air bubble detectors before and after the irradiation cassette and connected to the central control means for detecting the presence of air about to enter the treatment cassette. The presence of the air indicates evacuation of container 22 and signals the end of the first treatment pass. Thereafter, the central control means reverses the direction of blood pump 12 and draws blood from container 35 back through the treatment cassette through the blood pump and to container 22. The actual direction of the blood flow through the treatment cassette is of no significance as flow in either direction is equally photoactivated. An advantage gained by reversing direction (as opposed to constant cycling in the same direction) is the hydrodynamic mixing of blood as it is passed through the container. Such mixing is thought to result in a more thorough treatment of the individual cells because the statistical probability that each cell will be individually contacted by irradiation is increased. This process of blood flow until container 22 or 35 is emptied and then blood flow reversal, is continued until the desired exposure time is attained. At that point, the treated blood portion is then preferably returned to blood container 22 and the tubing set 24' discarded.

Container 22 is then ideally removed to stand 15 and a third tubing set connected to container 22 for reinfusion of the treated blood portion into the patient. During the second operational mode when the actual irradiation treatment is performed as depicted by FIG. 2, the patient is preferably disconnected from the machine thereby adding to his (or her) comfort level by permitting him freedom to move about but also concommitantly, increasing his safety level as he (or she) is not connected to the machine when the high voltages, necessary to drive the irradiation sources, is present.

To further decrease the risk of contamination to the patient blood and blood portions, each time a connection is made or broken, it is preferably only done once. Thus, container 22 would have three connection points to it; one for the first mode collection of the leukocyte enriched blood portion, one for the second mode treatment phase shown by FIG. 2, and the third for the third operational mode wherein treated blood is reinfused to the patient.

With particular reference to FIG. 3, the control panel 19 of the apparatus 10 is shown with the key board entry buttons 44 each ideally having a light 45 which, when lit, preferably indicates the stage of the operation. As will be noted, the key board entry buttons 44 are preferably placed in sequential order thereby assisting the operator in learning the system and performing the steps in the correct order. Indeed, the central control means will preferably be programmed to prevent out of step sequences from being attempted. Display 46 indicates the volume of leukocyte enriched blood collected in container 22. Although not shown, there is preferably also included a manual override switch contained within apparatus 10 such as behind access doors 18 (see FIGS. 1 and 2) for allowing an experienced operator to select any step out of sequence in the unlikely circumstance that such may be necessary to return all blood to the patient in the event of a machine failure.

The central portion of panel 19 contains power switch 51 as well as blood pump speed control 40 whereby the operator may select the speed with which the blood is withdrawn from the patient and pumped through the system during either collection or treatment phases. Also included, in the central section are lights 47 and 49. Alphanumeric display 49 indicates alarms and status regarding the machine's sequential operations. Status lights 47 are preferably provided in green, yellow, and red colors in order to provide at a glance the overall operating status of apparatus 10. Further included is a mute reset button 48 for quieting an audible alarm activated in the event an alarm condition occurs and operator input is required to correct a problem.

Other features may be readily apparent from the drawings such as the preferable inclusion of casters and caster brakes for enhancing the mobility of the apparatus. Further, upper access door 18 will preferably include mechanical means for assisting in the securement of containers 22, 23, 34, and 35. It may also optionally be outfitted with a transparent or translucent opening in the area beneath container 22 for providing at a glance information regarding the illumination status of the irradiation treatment cassette during the treatment phase. For instance, if the window is of sufficient size, the operator may readily determine that each irradiation source within the treatment cassette is illuminated as desired. Naturally, the material comprising such window is preferably selected in order to contain harmful radiation, if any, within apparatus 10.

Figure 4:
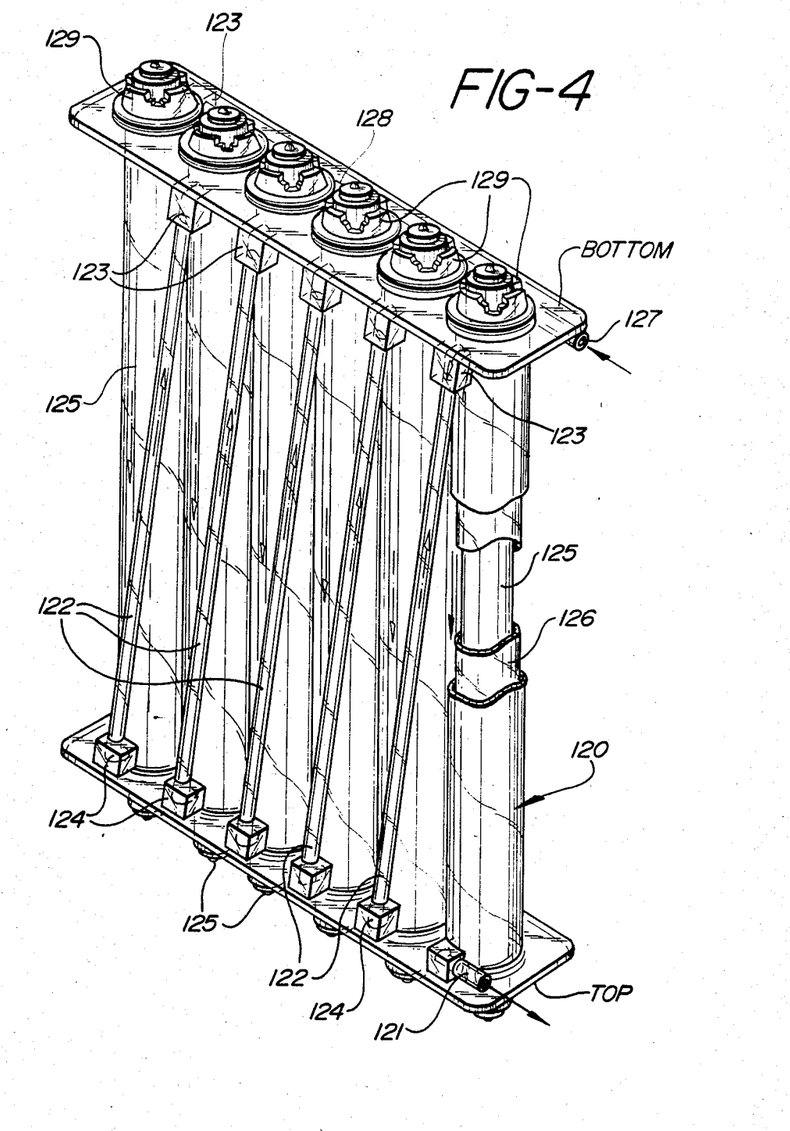
FIG. 4 shows the preferred embodiment of the irradiation cassette.
Figure 5:
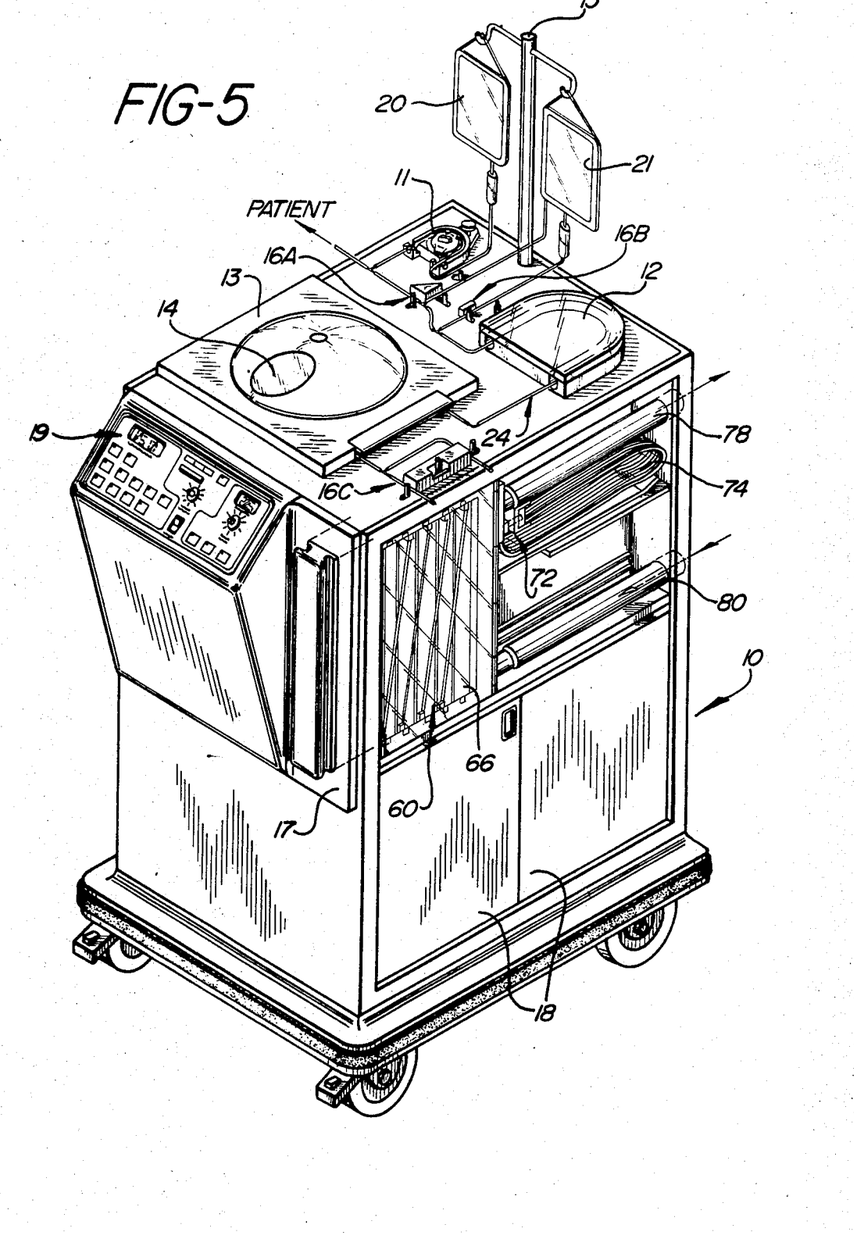
FIG. 5 shows a phantom view of the preferred cassette drawer assembly in closed position on the treatment system.
Figure 6:
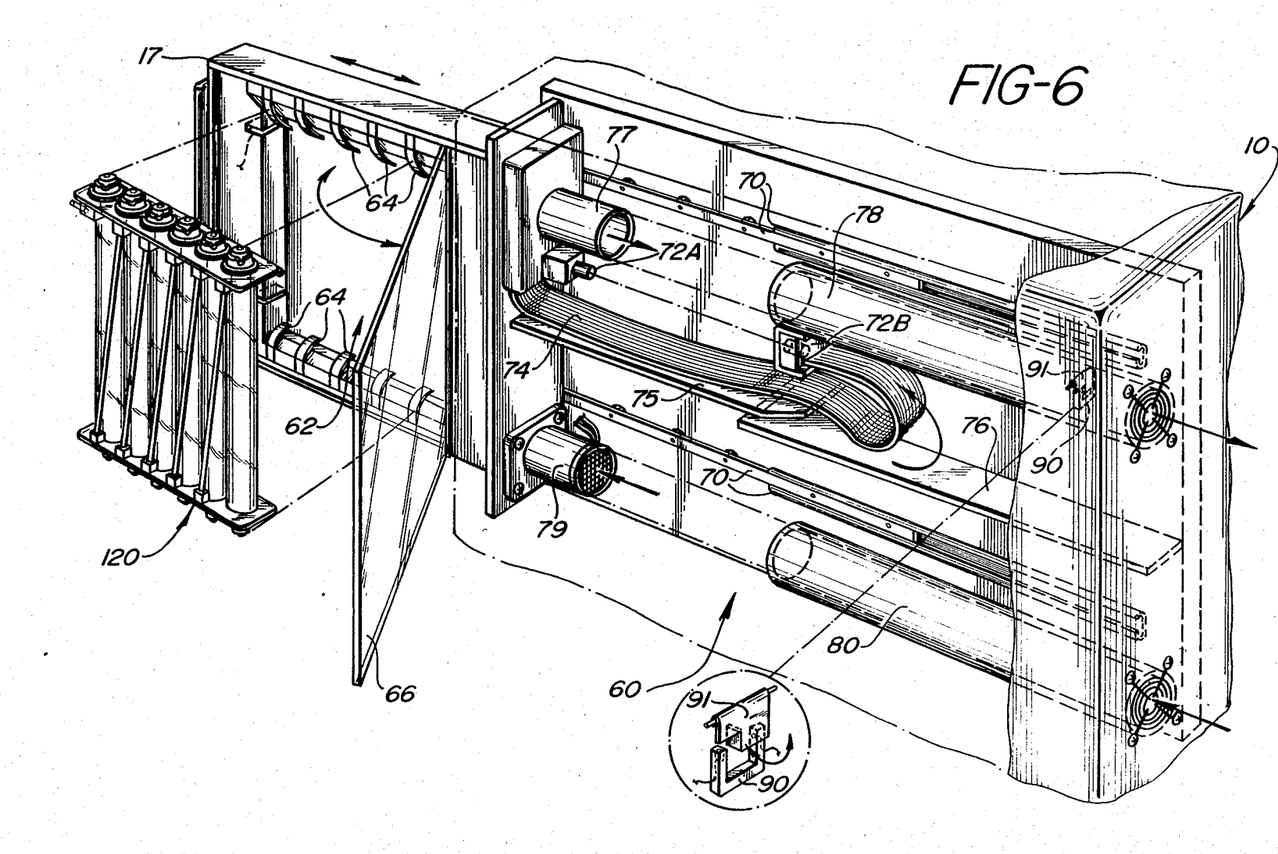
FIG. 6 shows an exploded view of the preferred cassette drawer assembly of the present invention in an open position.

FIGS. 5 and 6 reveal details of the cassette drawer assembly for the photoactivation patient treatment system described above and shown in FIGS. 1-3. FIG. 4 reveals details of the preferred irradiation treatment cassette of Taylor. Although the construction and operational details of this cassette are more fully explained in the copending Taylor application, a brief summary herein may be beneficial. The blood portion or leukocyte enriched blood enters the cassette at 121 and flows vertically between inner tube 126 and outer tube 120 which surrounds illumination tube 125. It is ejected from the first cavity through 123 flowing through connection tube 122 into entry port 124 for the next cavity. The serpentine flow is continued until final ejection occurs at 127. Tabs 129 serve to hold radiation source 125 in place as well as to allow for air flow in the space between 125 and inner tube 126. This air flow is ideally provided in order to ensure adequate cooling of the irradiation sources and avoid undesirable excess heating of the blood undergoing radiation treatment.

Referring now to FIG. 6, the treatment cassette 120 is contained within cassette drawer assembly 17 having electrical contact tabs 64 for contact with the irradiation sources. The drawer assembly 17 preferably has a side wall 62 and hinged wall 66 which, when closed after insertion of cassette 120, forms a closed box (along with the front, back, top and bottom walls) save for intake port 79 and exhaust port 77. Thus, air flowing into port 79 will, due to preferred construction of assembly 17 and cassette 120, be forced to flow through the cassettes inner cooling cavities having openings at the contact ends and thence out through exhaust port 77. Intake 79 further ideally comprises a motorized fan for forceably drawing air and thus by pressure inducing the inflow of cool air.

The drawer assembly 17 is ideally mounted on tracks 70 thereby allowing it to slide in and out of patient treatment apparatus 10. When pulled out of system apparatus 10, installation and removal of cassette 120 is facilitated and when closed, such as shown in FIG. 5, the entire irradiation treatment cassette is contained wholly within patient treatment system 10. Accordingly, it is preferred that intake 79 and exhaust 77 matably engage with extension tubes 80 and 78 respectively whereby cooling air may be obtained and ejected respectively from the outside of apparatus 10. Air flow is detected by movement of wind vane 91 which blocks or unblocks optical source/detector 90 which generates a signal communicated to analog circuit means not shown.

Cassette drawer assembly 17 further comprises a first power interconnect means 72a for matable engagement with second power interconnect means 72b whereby power may be supplied to the irradiation cassette 120 only when drawer assembly 17 is in the closed position. This arrangement ensures operator safety during the installation and removal steps of the treatment phase. Further, drawer assembly 17 has mounted on the back panel thereof, extension 75 having attached thereto braided ribbon wires 74 which connect to temperature sensors, bubble detectors, and interlock safety devices ideally contained within drawer assembly 17. Extension 75 slides along protector ledge 76 as drawer assembly 17 is closed thereby resulting in the safe coiling and storage of braided ribbon wire cable into the space contained between intake extension 78 and protector ledge 76. It is preferable that braided wires be used in the ribbon assembly as solid wires do not possess the necessary flexibility. Interconnect means 72a and 72b further comprise additional electrical contacts to ensure that when the drawer assembly is closed, it is closed completely and means 72a and 72b are fully engaged.

FIG. 5 shows a phantom view of the drawer assembly in the closed position within patient treatment apparatus 10. FIG. 5 shows how cooling air intake 80 receives air from outside the instrument, circulates it to drawer assembly 17 and then emits same through exhaust 78. Also shown is the engagement of power interconnect means 72 and storage of braided ribbon cable 74. In a most preferred embodiment, drawer 68 and panel 60, mounted on apparatus 10, will be of a transparent or translucent material so that, upon installation of upper door 18 (removed in FIG. 5), the operator may readily determine at a glance that all irradiation tubes within the irradiation cassette 120 are illuminated during the treatment phase.

What is claimed is:

1. In a patient treatment system for extracorporeally irradiating blood from said patient to photoactivate a reagent in contact therewith and wherein said blood is circulated through a plurality of serially connected, cylindrical cavities having a radiation source centrally disposed therein forming a treatment cassette, an apparatus for use in said treatment system and for receiving said cassette comprising:

a container formed from front and back panels connecting top and bottom panels and adapted to receive said cassette;

means for supplying electrical power to said radiation source of said treatment cassette, said means for supplying electrical power having first power interconnect means mounted on said container for matably engaging second power interconnect means mounted on said patient treatment system;

said container being movably mounted on tracks attached to said patient treatment system whereby said container must be moved to a first position to permit installation or removal of said cassette and where movement to said first position disengages said first power interconnect means from said second power interconnect means and wherein said container must be moved to a second position to engage said first and second means for supplying energy to activate said radiation source.

2. The cassette holding apparatus of claim 1 further comprising:

means for cooling said radiation sources including intake means mounted on said container for receiving air from said patient treatment system and exhaust means mounted on said container for discharging air to said patient treatment system, said intake and exhaust means being disengagable from said patient treatment system when said container is moved to said first position and reengagable upon movement of said container to said second position.

3. The cassette holding apparatus of claim 2 wherein said intake and exhaust means each comprise a hollow pipe communicating with said container and slidably engageable with mating counterparts on said patient treatment system.

4. The cassette holding apparatus of claim 1 wherein said cassette holding apparatus further comprises radiation sensor means for detecting whether said radiation source is activated upon engagement of said first and second power inteconnect means and temperature sensor means for detecting air flow through said container and further comprises blood temperature sensors and bubble detector sensors.

5. The cassette holding apparatus of claim 4 wherein said blood temperature and bubble detector sensors are connected to said patient treatment system by a plurality of braided ribbon wires fixedly mounted on an extension attached to the back panel of said container, said braided ribbon wires provided in excess to allow movement of said container to said first and second positions, said extension being juxtaposed near protector ledge means for containing and storing said braided ribbon wires in a safe location upon movement of said container to said second position.

* * * * *